US 6,613,507 B1

(12) United States Patent
Chang

(10) Patent No.: US 6,613,507 B1
(45) Date of Patent: Sep. 2, 2003

(54) BORAADAMANTANE COMPOUNDS FOR THE TREATMENT OF PATHOGENIC VIRUSES AND OTHER MEDICAL APPLICATIONS

(75) Inventor: Yu-An Chang, 3631 Hamilton St., Irvine, CA (US) 92614

(73) Assignee: Yu-An Chang, Irvine, CA (US)

( * ) Notice: Subject to any disclaimer, the term of this patent is extended or adjusted under 35 U.S.C. 154(b) by 125 days.

(21) Appl. No.: 09/813,249

(22) Filed: Mar. 21, 2001

Related U.S. Application Data
(60) Provisional application No. 60/190,885, filed on Mar. 21, 2000.

(51) Int. Cl.[7] .............................. C12Q 1/00; C07C 2/58
(52) U.S. Cl. ........................................... 435/5; 585/725
(58) Field of Search ............................ 435/5; 585/725

(56) References Cited

U.S. PATENT DOCUMENTS

| | | |
|---|---|---|
| 5,356,880 A | 10/1994 | Kurono et al. |
| 5,733,904 A | 3/1998 | Fujii et al. |
| 5,763,406 A | 6/1998 | Pedersen et al. |
| 5,849,800 A | 12/1998 | Smith |
| 6,037,348 A | 3/2000 | Colacina et al. |
| 6,136,835 A | 10/2000 | Camden et al. |
| 6,143,715 A | 11/2000 | Llinas-Brunet et al. |
| 6,194,430 B1 | 2/2001 | Camden et al. |

FOREIGN PATENT DOCUMENTS

SU          702022 A1  *  12/1979

OTHER PUBLICATIONS (a) Liang et al. Hepatology 18:1326–1333, (1993). (b) Tsukuma et al. N. Engl. J. Med. 328:1797–1801, (1993).
Ascher et al. Hepatology 20 (suppl.): 24–27, (1994).
Davis et al. N. Engl. J. Med. 321:1501–1506, (1989).
Di Bisceglie etal. N. Engl. J. Med. 321:1506–1510, (1989).
Tine etal. J. Hepatol. 13:192–199 (1991).
Taliani et al. Arch. Virol. Suppl. 4:294–298, (1992).
Poynard et al. N. Engl. J. Med. 332:1457–1462, (1995).
Smith J. P. Dig. Dis. Sci. 1997 Aug; 42(8):1681–7.
Parolin M. B. Ital. J. Gastroenterol Hepatol. Mar.; 1999 31(2):130–4.
Orth R. E. in Principles of Medicinal Chemistry, 2nd edition, p. 866–67. (Ed. Foye, W. O.) (1981). Published by Lea & Febiger; Philadelphia, PA.
Mathison I. W. et al. in Principles of Medicinal Chemistry, 2nd edition, p. 79–88. (Ed. Foye, W. O.) (1981). Published by Lea & Febiger; Philadelphia, PA.
Mathison I. W. et al. in Principles of Medicinal Chemistry 2nd edition, p. 81. (Ed. Foye, W. O.) (1981). Published by Lea & Febiger; Philadelphia, PA.
Aoki and Sitar, Clin. Pharm. 14:35–51, (1988).
Davies W. L. et al., Science, 144, 862 (1964).
Stromberg U. et al. J. Pharm. Pharmacol., 22, 959 (1970).
Di Bisceglie et al., Hepatology 16:649–654 (1992).
Mikhailov B. M. et al., Journal of Organometallic Chemistry, 219 (1981) 295–300.
Markushin S G et al., Vopr Virusol1993 May–Jun.; 38(3):122–6. (1993).
Keung, W., Silber, E., and Eppenberg, U. Anal. Biochem. 182: 358–369, 1989.
Denizot F., and Lang, R. J Immunol Methods, 89: 271–277, 1986.
Carmichael J., DeGraff, W.G., Gazdar, A.F., Minna, J.D., Mitchell, J.B. Cancer Res., 47: 936–942, 1987.

* cited by examiner

Primary Examiner—James Housel
Assistant Examiner—Stacy Brown
(74) Attorney, Agent, or Firm—Yu-An Chang

(57) ABSTRACT

Methods for treating patients with viral infections and Parkinson's disease with pharmaceutical agents are disclosed. In one embodiment, the viruses are Hepatitis C, Influenza A and B. The Pharmaceutical agents are 1-boraadamantane and the conjugate amines described in this patent application.

12 Claims, 4 Drawing Sheets

Figures, Table and Graphs:

Figures, Table and Graphs:

Boraadamantane Compound A Chemical Structure

Boraadamantane Compound B Chemical Structure

Boraadamantane Compound C Chemical Structure

BORAADAMANTANE COMPOUNDS FOR THE TREATMENT OF PATHOGENIC VIRUSES AND OTHER MEDICAL APPLICATIONS

This application claims the benefit of provisional application 60/190,885, filed Mar. 21, 2000.

TECHNICAL FIELD OF THE INVENTION

The present invention generally relates to a serial of boraadamantane compounds and their potential biological activities against pathogenic viruses as well as other medical applications. More particularly, these boraadamantane compounds which have general chemical structures shown in FIG. 1 are the pharmaceutical agents. The pathogenic viruses are Hepatitis C viruses, and Influenza A and B. Other medical applications include usage as dopamine agonists for the treatment of Parkinson's disease.

BACKGROUND OF THE INVENTION

Hepatitis C infection is associated with advanced liver disease (Liang, et al. Hepatology 18:1326–1333, (1993) and Tsukuma, et. al. The New England Journal of Medicine 328:1797–1801 (1993)), and liver failure due to hepatitis C infection is the most common indication for liver transplantation. Currently, the approved treatment for hepatitis C infection is α-interferon with or without combination of another pharmaceutical agents, e.g. ribavirin. However, many of those responding to these treatments will relapse upon discontinuation of the therapies (Davis, et al. The New England Journal of Medicine 321:1501–1506 (1989) and Di Bisceglie, et al. The New England Journal of Medicine 321:1506–1510 (1989)). Most of the patients who are retreated will again relapse if these drugs were withdrawn (Tine et al. Journal of Hepatology 13:192–199 (1991)). For those patients who do not respond to the initial interferon therapies, heavier dose treatments only produced little positive results. Significant increase of side effects has been observed on those patients treated with high dose regiments (Poynard et al. New England Journal of Medicine 332:1457–1462 (1995)). The low response rate and significant positive synergistic effect of combination of α-interferon with other pharmaceutical agent such as ribavirin have prompt investigators to search for other drugs which may be active against hepatitis C virus.

Smith J P (Digestive Diseases Sciences 1997 August; 42(8):1681–7) of Pennsylvania State University performed an open-labeled prospective pilot study to test the safety and efficacy of the antiviral drug, amantadine, in patients with chronic hepatitis C infection who had previously failed therapy with interferon-alpha 2b. Their clinical results indicated that amantadine improved both biochemical and virological markers in patients with hepatitis C who had previously not responded to treatment with interferon.

Brillanti S et al. (Italian Journal of Gastroentoerology and Hepatology 1999 March; 31(2):130–4) reported their pilot study evaluating the potential efficacy and safety of triple antiviral therapy in α-interferon non-responders. Patients with chronic hepatitis C who had failed to respond to a 6 month course of α-interferon were randomly assigned to receive two different types of therapies (double therapy or triple therapy) for 6 months. Double therapy: combination of α-interferon+oral ribavirin. Triple therapy: same combination+oral amantadine (1-adamantanamine hydrochloride; Symmetrel; see chemical structure in FIG. 2). The clinical results indicated that: Triple therapy seems to be able to induce biochemical and virological responses significantly better than the double therapy. Triple therapy also sustained these antiviral responses longer than the double therapy.

Amantadine Hydrochloride, N. F. (Orth R. E. in "Principels of Medicinal Chemistry, $2^{nd}$ edition, page 866–867. Ed. Foye, W. O. (1981)) has been approved by the FDA for the treatment of influenza A2 infection. It is active against influenza A, A1 and A2, Sendai and rubella viruses. Amantadine (Neumeyer J. L. in Principles of Medicinal Chemistry, $2^{nd}$ edition, page 248–249. Ed. Foye W. O. (1981)) also has clinically significant anti-parkinsonian effects. It appears to increase the release of dopamine and enhance accumulation of brain dopamine with fewer side effects than levodopa or the anticholinergic drugs.

Langmuir (Mathison I. W. et al. in Principles of Medicinal Chemistry $2^{nd}$ Edition, page 79–88. Ed. Foy W. O. (1981)) originated the concept of chemical isosterism. He elaborated upon the similarities in physicochemical properties of atoms, groups, radicals and molecules with similar electronic structures. Table 1 is a comparison of the physical properties of $N_2O$ and $CO_2$ and illustrates some of the data compiled by Langmuir; similar relationships have been shown for $N_2$ and CO. Hinsberg first proposed the isosteric replacement of CH=CH by S and recognized the interchanging of the various aromatic rings, such as thiophene, benzene, pyridine, pyrrole and furan as isosteric group replacements.

Chemical isosterism when applied in the drug design and molecular modification in the creation of new and improved therapeutic agents was termed "bioisosterism" by Friedman. The classic monovalent bioisostereomers included the halogens and the groups —XHn, where X is C, N, O, and S; n=1 to 3. The divalent atoms and groups are R—O—R', R—NH—R', R—$CH_2$—R' and R—$SiH_2$—R'. The trivalent bioisosteres include R—N=R' and R—CH=R'. Tetrsubstituted atoms are: =C=, =$N^+$=, and =$P^+$=. The group relating to ring equivalents includes the interchange of —CH=CH—, —S—, —O—, —NH, and —$CH_2$—.

FIGS. 3 and 4 show examples of bioisosteric applications in pharmaceutical agents. For example, both phenylephrine and alkylsulfonamidophenethanolamine (FIG. 3) have same medicinal effect, i.e. cause a 20% increase in blood pressure of the thiopental-barbital anesthetized dog. Diethylstilbestrol and the natural hormone estradiol (FIG. 4) have the same potency of estrogenic activities.

Boraadamantane compounds of this invention (FIG. 1) and amantadine (FIG. 2) are unique and new type of bioisostereomers. There are two different types of bioisosteric replacement. First, a boron atom replaces one carbon atom. Second, the covalent bond between carbon atom and nitrogen atom is replaced by a boron/nitrogen coordinate bond. In aqueous solutions, since amantadine has a pKa of 10.8, over 90% of the amino group of amantadine molecules will be protonated at physiological pH (pH 7.4). The amantadine molecules will carry a permanent positive charge while Boraadamantane compounds of this invention have a partial positive charge on the nitrogen atom and partial negative charge on boron atom. Thus they should be able to penetrate through the lipophilic cell membrane and the blood brain barrier easier than amantadine. Consequently, their anti-viral effects as well as anti-parkinsonian effects potentially will be better than amantadine. Similarity of their rigid chemical structures gives them two steric features, i.e. geometric and conformational isomerism. Thus, enhance the similarity of their pharmacological activities.

Organo-boron compounds are known to have relatively low toxicity. Carborane compounds with multiple boron atoms in the molecules have been intensely studied for boron neutron capture therapy. They have been studied for the treatment of various cancers for decades (Miura M. et al. The British Journal of Radiology, 71(1998), 773–781). Thus boraadamantane compounds of this invention which have only one boron atom per molecule should have minimum toxicity if there is any.

In summary, due to the chemical structure similarity of the Boraadamantane compounds of this invention (FIG. 1) and the known drug amantadine, the Boraadamantane compounds of this invention (FIG. 1) can be used for the treatment of various diseases caused by virus infections as well as Parkinson's disease with little or no serious side effects. These compounds can be used alone or in combination with other pharmacological agents such as alpha-interferon, ribavirin, etc.

SUMMARY OF THE INVENTION

BRIEF DESCRIPTION OF THE DRAWINGS

Additional objects and features of the present invention will become more apparent and the invention itself will be best understood from the following Detailed Description of Exemplary Embodiments, when read with reference to the accompanying Figures, and Tables.

DESCRIPTION OF THE INVENTION

Figure 1:
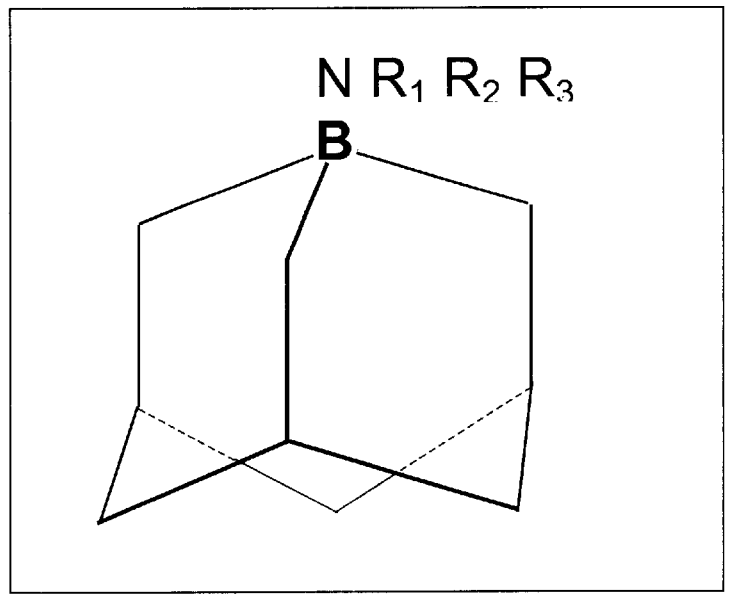
FIG. 1 is a schematic diagram of the general chemical structure of Boraadamantane compounds of this invention. While the amine conjugates (:$NR_1R_2R_3$) can be amino acids, peptides, proteins, and other non-toxic natural and synthetic amines.
Figure 2:
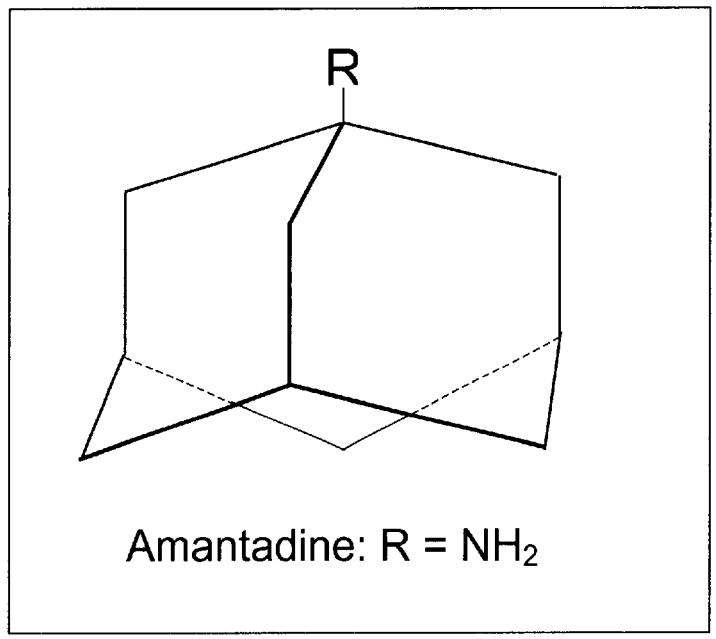
FIG. 2 is a schematic diagram of the chemical structure of amantadine (1-adamantanamine).
Figure 3A:
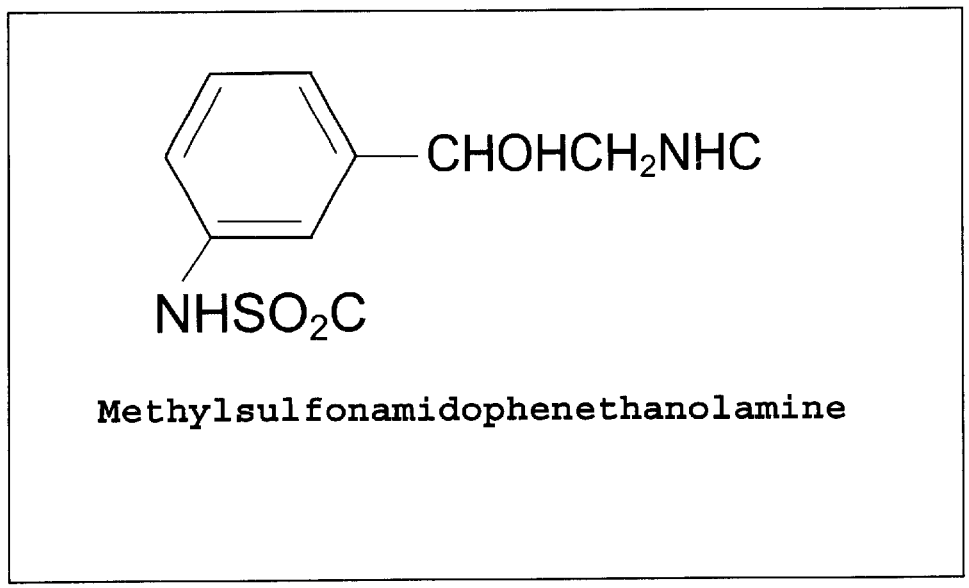
FIG. 3a is a schematic diagram of the chemical structure of methyl-sulfonamidophenethanolamine and FIG. 3b is a schematic diagram of the chemical structure of phenylephrine which illustrates their similarity in chemical structures and pharmacological effects.
Figure 3B:
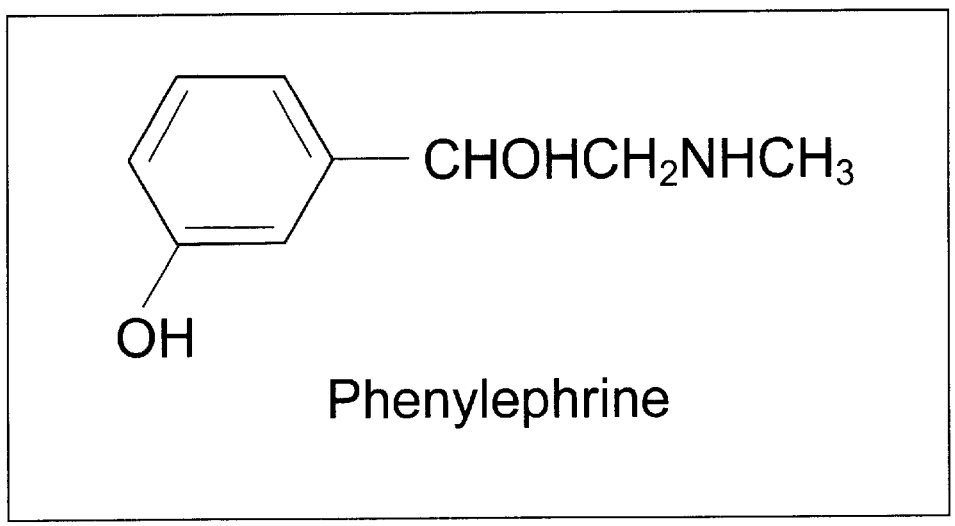
Figure 4A:
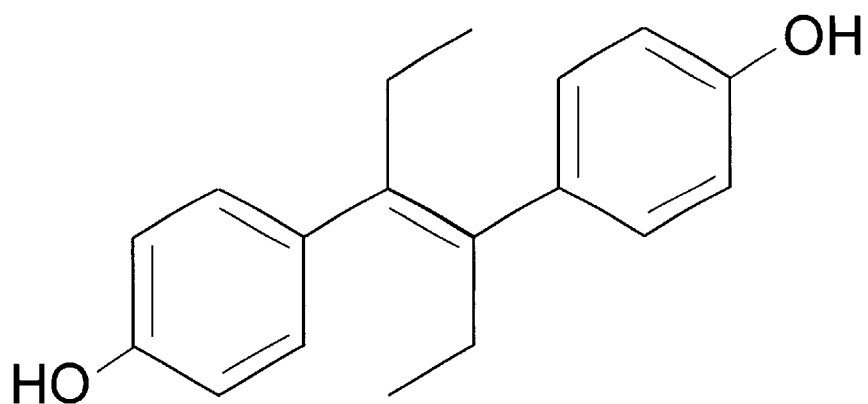
FIG. 4a is a schematic diagram of the chemical structure of Diethylstilbestrol.
Figure 4B:
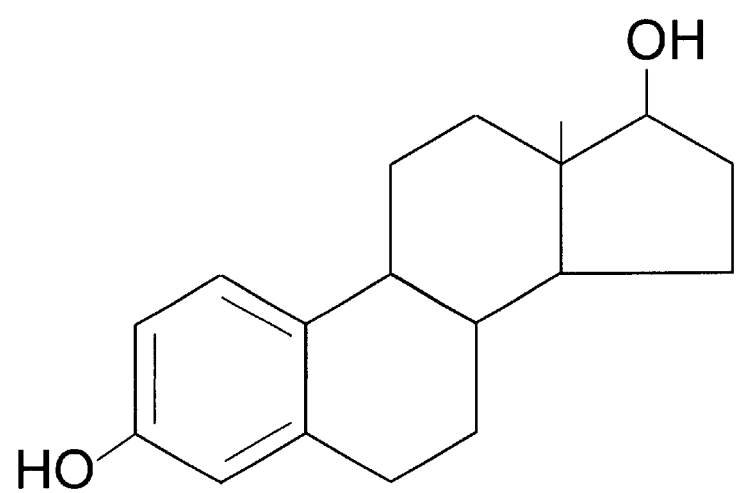
FIG. 4b is a schematic diagram of the chemical structure of the natural hormone estradiol which illustrate their similarity in chemical structures and medicinal effects.

The present invention contemplates the treatment of patients with viral infections or Parkinson's disease using the pharmaceutical agents—Boraadamantane compounds of this invention (FIG. 1). In one embodiment, the pharmaceutical agents of the present invention are cyclic 1-boraadamantane conjugates with amino acids, peptides, other synthetic or natural amines or proteins. In one embodiment, the viral infections are Hepatitis C and Influenza A and B or, Sendai and rubella viruses. In one embodiment, the patients with Parkinson's disease.

Amantadine has been approved by the FDA for the treatment of influenza A2, Sendai and rubella viruses infections and Parkinson's disease (Aoki F. Y. et al. Clinical Pharmacokinetics 1988 January; 14(1):35–51). Although the exact mechanism is unnecessary to carry out the methods of the present invention, it is believed that amantadine interferes with viral replication by inhibiting the uncoating of the influenza virus. It also prohibits viral genome penetration into the host cells (Davis, W. L. et al. Science, 144, 862–863 (1964)). Amantadine also is believed to increase the release of dopamine and to cause the inhibition of the membrane pump which resulting in the enhanced accumulation of brain dopamine (Stromberg U. et al. Journal of Pharmacy and Pharmacology, 22, 959 (1970)). Amantadine also produced fewer side effects than levodopa or the anticholinergic drugs. Due to the chemical structure similarity, Boraadamantane compounds of this invention can have same mechanism and biological effects as amantadine.

Treatment with Boraadamantane compounds of this invention offers several implied advantages over other treatment schemes, for example, interferon. The oral route, thus potentially improving patient safety and compliance, can administer them. Amantadine is fairly well tolerated with few side effects; therefore, Boraadamantane compounds of this invention (FIG. 1) can have same advantages as amantadine due to their chemical structure similarity.

Since interferon, corticosteroids or ribavirin (Di Bisceglie, A. M. et al., Hepatology 16:649–654 (1992)) have been shown to lower ALT levels in patients with HCV infection without altering HCV RNA level, these results indicate that these treatments are useful for treating the inflammatory response in the liver to Hepatitis C infection, but do not treat the infection itself Conversely, amantadine has been shown to be able to reduce both ALT levels and HCV RNA replication. Therefore, Boraadamantane compounds of this invention (FIG. 1) can have same implied advantages due to their chemical structure similarity.

The present invention is not limited by the nature of the prior treatment of the patients, it is contemplated that the present invention be used in both naive patients (those have not been treated before) and those have not responded to interferon or other treatments as well as patients failed to respond to interferon retreatment or dose escalation.

Since amantadine does not depress leukocyte counts or significantly augment immunity, in one embodiment the present invention is used in patients with leukopenia, autoimmune diseases or organ transplants in addition to HCV. Unlike interferon, in one embodiment, the present invention can be used without age limitation such as children under eighteen year-old with HCV. Boraadamantane compounds of this invention (FIG. 1) can have same applications as amantadine due to their chemical structure similarity.

The present invention is not limited by the method of administration. In one embodiment, it is by conventional means available for use in conjunction with pharmaceuticals; either in combination with one another or in combination with other therapeutic agents. These include, but not limited to, antiviral agents, such as interferon or ribavirin. It is contemplated that the methods of the present invention be administered alone or can be administered with a pharmaceutical carrier selected on the basis of the chosen route of administration and standard pharmaceutical practice.

In one preferred embodiment, Boraadamantane compounds of this invention is administered orally in solid dosage forms, such as capsules, tablets, or powders, or in liquid dosage forms, such as syrups and suspensions; however, it can also be administered parenterally, in sterile liquid dosage forms, or rectally in the form of suppositories.

One skilled in the art will be capable of adjusting the administered dose depending upon known factors such as the mode and route of administration; age, health, and weight of the recipient; nature and extent of symptoms, kind of concurrent treatment, frequency of treatment, and the effect desired. In one embodiment, the dosage is increased to overcome a non-responsive condition.

Additionally, Boraadamantane compounds of this invention can be employed in admixture with conventional excipients, i.e., pharmaceutically carrier substances suitable for parenteral (e.g., topical application) or enteral (e.g., oral) which do not deleteriously react with the active compounds.

Suitable pharmaceutically acceptable carriers include but are not limited to water, salt solutions, alcohols, gum arabic, vegetable oils, benzyl alcohols, polyethylene glycols, gelatine, carbohydrates such as lactose, amylose, or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, merely to name a few. The pharmaceutical preparations can be sterilized and if desired mixed with auxiliary agents, e.g., lubricants, preservatives, stabilizers, wetting agents, emulsifier, salts for influencing osmotic pressure, buffers, coloring, flavoring, and/or aromatic substances and the like which do no deleteriously react with the active compounds. They can also be combined where desired with other agents, e.g. vitamins and other nutrients.

For enteral application, particularly suitable are tablets, liquids, drops, suppositories, or capsules. A syrup, elixir, or the like can be used wherein a sweetened vehicle is employed. Control-release or directed release compositions can be formulated, e.g., liposomes or those wherein the active compound is protected with differentially degradable coating, e.g., by microencapsulation, multiple coatings, etc.

In this manner, the present invention may be introduced into a subject in polymeric microspheres for the control-release of the compound. For parenteral application, particularly suitable are injectable, sterile solutions, preferably oily or aqueous solutions, as well as suspensions, emulsions, or implants including suppositories. Nebulizers and inhalation aerosols may also be used. Ampoules are in convenient unit dosages. It is also possible to freeze-dry the new compounds and use the lyophilizates obtained, for example, for the preparation of products for injection. For other parenteral applications, such as topical applications, viscous to semi-solid or solid forms comprising a carrier compatible with topical application and having a dynamic viscosity preferably greater than water. Suitable formulations include but are not limited to transdermal patches, solutions, suspensions, emulsions, creams, ointments, powders, liniments, salves, aerosols, etc., which are, if desired, sterilized or mixed with auxiliary agents, e.g., preservations, stabilizers, wetting agents, buffers, or salts for influencing osmotic pressure, etc.

Also suitable for topical application are sprayable aerosol preparations wherein boraadamantane compounds of this invention, preferably in combination with a solid or liquid inert carrier material, are packaged in a squeeze bottle or in admixture with pressurized volatile, normally gaseous propellant, e.g., a freon. The application of these embodiments can be to the skin or mucous membrane or in the interior of the body and can be oral, enteral, pulmonary, rectal, nasal, vaginal, lingual, intravenous, intraarterial, intramuscular, intraperitoneal, intracutaneous, subcutaneous. The parenteral preparations are preferably sterile or sterilized products.

Other medicaments containing boraadamantane compounds of this invention can be produced in a known manner, whereby the known and customary pharmaceutical adjuvants as well as other customary carrier and diluting agents can be used. Examples include, but are not limited to, gelatins, natural sugars such as sucrose or lactose, lecithin, pectin, starch (for example cornstarch), alginic acid, tylose, talc, lycopodium, silica (for example colloidal silica), glucose, cellulose, cellulose derivatives for example, cellulose ethers in which the cellulose hydroxyl group are partially etherified with lower aliphatic alcohols and/or lower saturated oxyalchohols, for example, methyl hydroxypropyl cellulose, methyl cellulose, cellulose phthalate, stearates, e.g., methylstearate and glyceryl stearate, magnesium and calcium salts of fatty acids, especially saturated acids (for example, calcium stearate, calcium laurate, magnesium oleate, calcium palmitate, calcium behenate and magnesium stearate), emulsifiers, oils and fats, especially of plant origin (for example, peanut oil, castor oil, olive oil, sesame oil, cottonseed oil, corn oil, wheat germ oil, sunflower seed oil, cod-liver oil), mono, di, and triglycerides of fatty acids, e.g. glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400, and other polyethylene glycols, as well as derivatives of such alcohols and polyglycols, esters of saturated and unsaturated fatty acids (2 to 22 carbon atoms, especially 10 to 18 carbon atoms), with monohydricaliphatic alcohols (1 to 20 carbon atom alkanols), or polyhydric alcohols such as glycols, glycerine, diethylene glycol, pentaerythritol, sorbitol, mannitol, ethyl alcohol, butyl alcohol, octadecyl alcohol, etc., e.g. glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case be etherified, benzyl benzoate, dioxolane, glycerine formal, tetrahydrofurfuryl alcohol, polyglycol, dimethyl acetamide, lactamide, lactates, e.g., ethyl lactate, ethyl carbonate, silicones (especially middle viscosity dimethyl polysiloxane)

Other adjuvants can also be substances which bring about decomposition (so-called explosives) such as: cross-linked polyvinyl pyrrolidone, sodium carboxy methyl starch, sodium carboxy methyl cellulose or microcrystalline cellulose. Likewise, known coating agents such as e.g. polyacrylates, cellulose ethers and the like can be used. For the production of solutions, there can be used water of physiologically compatible organic solvents, as for example, ethanol, 1,2-propylene glycol, polyglycols, e.g., diethylene glycol, triethylene, glycol and dipropylene glycol and their derivatives dimethyl sulfoxide, fatty alcohols, e.g., stearyl alcohol, cetyl alcohol, lauryl alcohol and oleyl alcohol, triglycerides, e.g. glyceryl olelate glyceryl stearate, glyceryl palmitate, and glyceryl acetate, partial esters of glycerine, e.g., glyceryl monostearate, glyceryl distearate, glyceryl monopalmitate, paraffins, and the like.

For injectable solutions or suspensions, non-toxic parenterally compatible diluting agents or solvents can be used, for example: Water, 1,3 butane diol, ethanol, 1,2-propylene glycol, polyglycols in a mixture with water, Ringer's solution, isotonic solution of sodium chloride or also hardened oils including synthetic mono or diglycerides or fatty acids like oleic acid.

Known and customary solution assistants or emulsifiers can be used in the production of the preparations. The following are examples of solution assistants and emulsifiers which can be used: Polyvinylpyrrolidone, sorbitan fatty acid esters such as sorbian trioleate, phosphatides such as lecithin, acacia, tragacath, polyoxethylated sorbitan monooleate and other ethoxyated fatty acid esters of sorbitan, polyoxyethylated fats, polyoxyethylated oleotriglycerides, linolized oleotriglycerides, polyethylene oxide condensation products of fatty alcohols, alkyl phenolene or fatty acids or also 1-methyl-3-(2-hydroxyethyl) imidazolidone-(2). The term polyoxyethylated means in this context that the substances in question contain polyoxyethylene chains whose polymerization is generally between 2 to 40 and especially between 10 to 20.

Furthermore, there can be added preservatives stabilizers, buffers, for example, calcium hydrogen phosphate, colloidal aluminum hydroxide, taste correctives, antioxidants and complex formers (for example, ethylene diamine tetraacetic acid) and the like. In a given case for stabilization of the active molecule, the pH is adjusted to about 3 to 7 with physiologically compatible acids or buffers. Generally, there is preferred as neutral as possible to weak acid (to pH 5) pH value.

As antioxidants, there can be used, for example, sodium meta-bisulfite, ascorbic acid, gallic acid, alkyl gallates, e.g., methyl gallate and ethyl gallate, butyl hydroxyanisole, nordihydroguararetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives, there can be used, for example, sorbic acid, p-hydroxybenzoic acid esters (for example, lower alkyl esters such as the methyl ester and the ethyl ester) benzoic acid, sodium benzoate, trichloroisobutyl alcohol, phenol, cresol, benzethonium chloride, and formalin derivatives.

Figure 5:
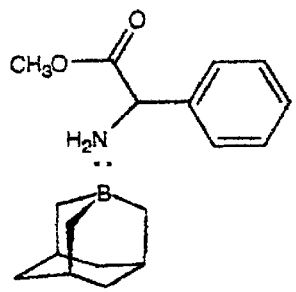
FIG. 5 is a schematic diagram of the chemical structures of Boraadamantane compound A, B and C of this Invention.
Figure 5:
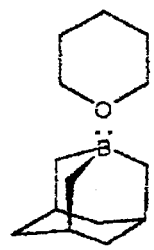
Figure 5:
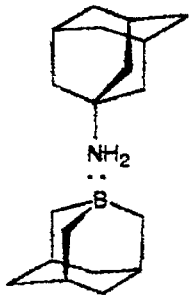

The following examples are used to particularly point out the biological activities of the Boraadamantane compounds of this invention (FIG. 5) against HCV. Preparation of the Boraadamantane compounds of this invention use the methods published by Mikhailov B. M. et al. in Journal of Organometallic Chemistry 219 (1981) 295–300 and 260 (1984) 17–23 and the articles cited in these references.

EXAMPLE 1

Binding Affinity of Boraadamantane Compound A to CD81 Receptor

Boraadamantane compound A (5 $\mu$M) was tested for activity against C6 glioma cells and rat pup astrocyte cells. The assay was performed in 1% DMSO media. The results are expressed in % growth of untreated cells. The results for C6 glioma cells were 77.6% and for rat pup astrocyte cells 56.5%. These results demonstrated compound A has activity against CD81 containing rat pup astrocyte cells. Although it also inhibited cell growth of C6 glioma cells, which do not contain CD81 receptors, the inhibition was significantly less. These experimental results clearly demonstrated that compound A can bind to CD81 receptors and significantly reduced the cell growth. It is known that HCV virus also bind to CD81 receptors in order to enter the host cells, therefore, compound A can bind to CD81 receptors and prevent HCV virus from entering into the host cells.

EXAMPLE 2

Binding Affinity of Boraadamantane Compound A, B and C to CD81 Receptors

Boraadamantane compound A, B and C (5 $\mu$M) was tested for activity against C6 glioma cells and rat pup astrocyte cells. The assay was performed in 1% DMSO media. The results are expressed in % growth of untreated cells. The results for C6 glioma cells and for rat pup astrocyte cells were summarized in the following Table 2. Again, these results demonstrated compound A have significant differential antiproliferative activity against CD81 positive rat pup astrocyte cells vs. the C6 Glioma cells as previously seen. These results indicated the experiments are reproducible. Although compound C was not as active as compound A, compound C also inhibited cell growth of rat pup astrocyte cells, without inhibition of C6 glioma cell growth. Compound B did not show cell growth inhibition for both C6 glioma and rat pup astrocyte cells, since Compound B has an oxygen-boron instead of nitrogen-boron coordinate bond. These results strongly support the "bioisosterism" drug design concept of this invention.

These experimental results clearly demonstrated that compound A and C can bind to CD81 receptors and significantly reduced the cell growth. Thus they may prevent HCV virus from entering into host cells, consequently, they can be used as anti-HCV drugs. Also, reproducible experimental results were obtained, thus strengthen the proof of concept of this invention.

EXAMPLE 3

Anti-influenza A Activity of Compound B

Markushin et al. (Vopr Virusol 1993 March–June; 28(3):122–6) tested compound C against influenza type A and B viruses. Compound C was shown to inhibit multiplication of a wide range of influenza type A and B strains. Compound C also inhibits in cell culture the replication of a mutant of fowl plague virus A/FPV/Weibridge which was resistant to remantadine (a anti-influenza A drug). Compound C was found to exert a marked viricidal effect, to inhibit the hemolytic activity of both influenza A and B viruses. It disturbed virus specific proteins in influenza B/Ann Arbor/86-infected cells. From these results, due to the similarity of the chemical structures and bioisosterism, boraadamantane compounds of this invention should have similar anti-Influenza A and B activities.

EXAMPLE 4

Effect of Compound A Upon the Cell Viability and Proliferation of Human Cell Line Two assays were used to test the effect of compound A upon human cell line. Crystal violet assay (Kueng, W. et al. Analytical Biochemistry 182:16–19 (1989)) was used to evaluate the effect upon cell proliferation and MTT assay (Denizot F., et al. Journal of Immunological Methods 89:271–277 (1986) and Carmichael J. et al. Cancer Research 47:936–942 (1987)) for cell viability.

The test procedure was described as following:
Culture the cells in the tissue culture incubator at 37° C., 5% $CO_2$ for three days then removed the growth media. Add 5 mL releasing solution and incubated at 37° C. for 5 min.
1. To each well added undetermined cells/100 uL growth media for a few days. Checked under the microscope that the cells did not reach confluence-state.
2. Prepare Compound A Stock solution in DMSO as following: 4.8 mg Compound A dissolved in 1.6 mL DMSO. The concentration is: $100 \times 10^2$ uM (2,000× stock solution for 5 uM Test solution). This stock solution was serially diluted with 1.0% DMSO/Growth media to final concentration of 10, 5, 2.5 and 1.25 uM in 1% DMSO/Growth media.

3. To the wells were added Compound A (10 uM, 5 uM, 2.5 uM and 1.25 uM in 1% DMSO; 8 wells per concentration and to one control (8 wells) added only growth media solution, another 24 wells control only Growth media+1% DMSO.
4. The cells were incubated in the tissue culture incubator for 2 days and tested for Crystal Violet cell proliferation and MTT cell viability assays.

The Crystal Violet assay and MTT assay were performed following the procedure:

Crystal-Violet Stain Assay for Cell Proliferation:

Cells are plated at 2,000 cells/well in 96 well plates.

One day after plating, media is changed and drug or drug vehicle additions are made to respective wells.

Two days after addition, wells are drained and washed 3 times with 200 µL PBS.

Cells are fixed at 25° C. for 30 min. by the addition of 50 µL of 5% glutaraldehyde in PBS. Wells are washed 3 times with 200 µL water and are allowed to dry.

Cells are stained at 25° C. for 30 min. with 50 uL of a 1:1 (v:v) mixture of 0.2% (w/v) crystal violet and 100 mM CAPS (pH 9.0).

Wells are washed 3 times with 200 µL water and are allowed to dry.

Dye is solubilized by the addition of 50 µL/well of 10% (v/v) acetic acid.

Absorbance of all wells at 590 nm is determined using a plate reader.

Absorbances obtained in this way correlate with cell number up to 40,000–50,000 cells/well.

For growth curve analysis, multiple plates of each cell to be analyzed are initially made.

One day after plating, one plate is fixed and stained to obtain 0 time cell numbers.

On desired days post treatment, one plate is fixed and stained to obtain cell numbers for that day.

MTT Assay for Cell Viability:

Media of cells growing in 96 wells plates is changed to 100 µL serum-free, phenol red-free MEM.

To each well is added 10 µL of 5 mg/ml MTT (3-[4,5-dimethylthiazol-2-yl]-2,5-diphenyltetrazolium bromide), in PBS.

Cells are incubated with the MTT for 3–4 h at 37° C.

Wells are washed 4 times with 200 µL PBS.

Cells are solubilized with 100 µL 0.1 N HCl in isopropanol.

Absorbance of all wells at 590 nm is determined using a plate reader.

All color produced is due to the presence of viable cells.

Cell numbers will be obtained for treated cells, as described above.

The ratio of cell number to MTT absorbance will be examined using a standard curve (below) to assess the presence of dead cells in the crystal violet-binding population.

A standard curve will be made using a series of wells containing normally growing cells at various densities, and determining the cell numbers and MTT turnover in wells of same density.

The experimental results are summarized in graph A and B. Both Crystal Violet and MTT assay results indicated that Compound A at the concentration of 5 µM did not affect the cell viability and proliferation. Thus this in vitro experiment data suggested that Boraadamantane compound A of this invention, at the concentration of 5 µM has minimal toxicity, if there is any upon human cell line.

What is claimed is:

1. A method of treating HCV viral infections in human patients, comprising:

a) providing:
        i) a patient infected with Hepatitis C, and
        ii) a formulation consisting of Boraadamantane compounds as in FIG. 1 alone or in combination with other pharmaceutical agents, wherein R1, R2 and R3 are selected from the group consisting of amino acids, peptides, proteins, and other non-toxic natural and synthetic amines; and b) Administering a dose of said formulation in a dosage level from about 0.01 mg/kg/day to about 1000 mg/kg/day of body weight.

2. The method of claim 1, wherein said boraadamantane compounds consist of 1-boraadamantane and a conjugate base of twenty three natural amino acids and their derivatives.

3. The method of claim 1, wherein said boraadamantane compounds consist of 1-boraadamantane and a conjugate base of non-toxic peptides and their derivatives.

4. The method of claim 1, wherein said boraadamantane compounds consist of 1-boraadamantane and a conjugate base of proteins.

5. The method of claim 1, wherein said boraadamantane compounds consist of 1-boraadamantane and a conjugate base of other natural or synthetic non-toxic amines.

6. The method of claim 1, wherein said administering is enteral administration.

7. The method of claim 6, wherein said enteral administration is oral administration.

8. The method of claim 7, wherein said enteral administration utilizes control release technology.

9. The method of claim 1, wherein said administering is parenteral administration.

10. The method of claim 9, wherein said parenteral administration is subcutaneous administration.

11. The method of claim 9, wherein said parenteral administering utilizes an aerosol.

12. The method of claim 1, wherein said other pharmaceutical agents include alpha-interferon, ribavirin and other anti-HCV viral agents.

* * * * *